United States Patent [19]

Heeny et al.

[11] Patent Number: 5,077,194
[45] Date of Patent: Dec. 31, 1991

[54] RAPID STICK TEST FOR THE DIAGNOSIS OF BOVINE LEUKEMIA VIRUS INFECTION FROM SERUM OR MILK

[75] Inventors: Jonathan L. Heeny, Islington; Victor E. O. Valli, Guelph, both of Canada

[73] Assignee: University of Guelph, Guelph, Canada

[21] Appl. No.: 211,769

[22] Filed: Jun. 27, 1988

[51] Int. Cl.$^5$ .............................................. C12Q 1/70
[52] U.S. Cl. ........................................ 435/5; 435/7.1; 435/810; 436/528; 436/530; 436/532; 436/810
[58] Field of Search ............... 436/810, 528, 530, 532; 435/5, 7.1, 810

[56] References Cited

U.S. PATENT DOCUMENTS

| | | | |
|---|---|---|---|
| 4,816,392 | 7/1990 | Hokama | 435/805 |
| 4,842,995 | 6/1989 | Iaccheri et al. | 436/810 |
| 4,853,325 | 8/1989 | Vodian et al. | 436/810 |

Primary Examiner—Sam Rosen
Attorney, Agent, or Firm—Bell, Seltzer, Park & Gibson

[57] ABSTRACT

A method for the detection of the presence of anti-viral or anti-bacterial antibodies in a specimen and a kit for the same. The method comprises the use of a solid phase support dipstick having attached thereto suitable antigen-binding material to which viral antigens or bacterial antigens are bound. The antibodies specific for the bound antigens bind to the antigen and a second-antibody labelled with a means for visually detecting those antibodies which have formed immunocomplexes with the bound nitrogen when in the presence of suitable reactive agents. Also, a method of using such a dipstick in this method and in the test kit is disclosed. Specifically, boving leukemia virus is tested for; a dipstick attached to a removable closure is employed; and the dipstick has two antigen binding areas, one of which is a control.

20 Claims, 1 Drawing Sheet

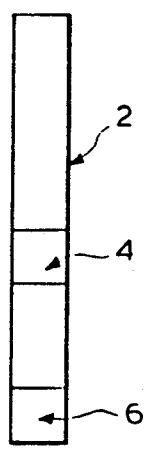
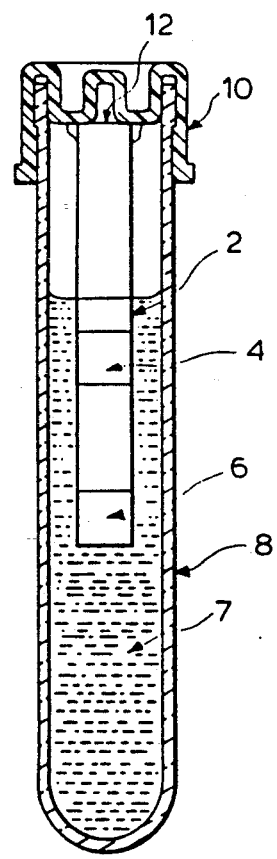
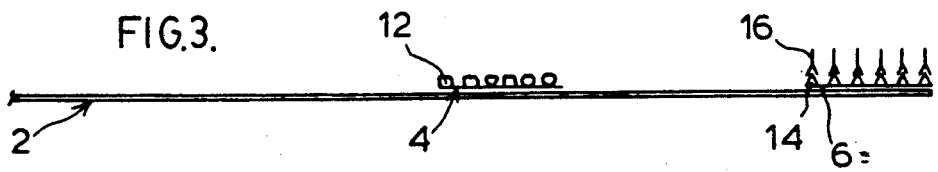
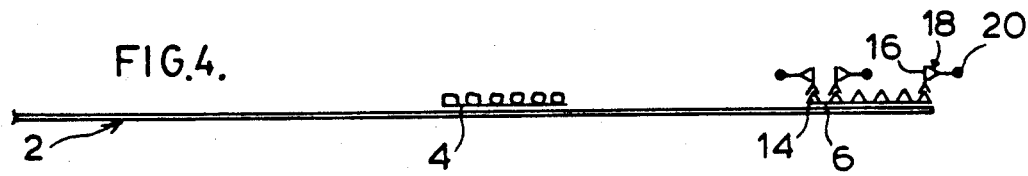
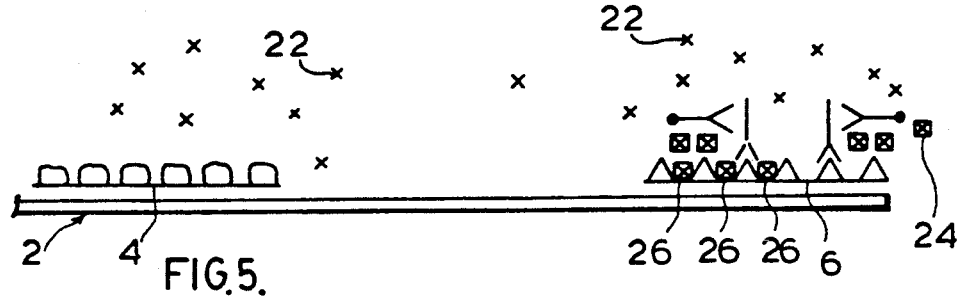

RAPID STICK TEST FOR THE DIAGNOSIS OF BOVINE LEUKEMIA VIRUS INFECTION FROM SERUM OR MILK

FIELD OF THE INVENTION

This invention relates to a method for the rapid detection of the presence of anti-viral and antibacterial antibodies in a specimen such as serum or milk and the corresponding kit for the rapid detection of these antibodies.

BACKGROUND OF THE INVENTION

The control of bovine leukemia virus (BLV) in dairy herds is important in terms of economic loss from export restrictions and carcass condemnation at slaughter in cases which eventually develop lymphoma.

Diagnostic tests for BLV infection include various enzyme-linked immunosorbant assays (ELISA), radio-immunoassays (RIA), and agar gel immunodiffusion (AGID) tests against various viral antigens, as well as viral isolation and viral neutralization tests (Burny et al., 1980, in Klein, G., ed. *Viral Oncology*, New York: Raven Press, 231-89). The internationally recognized standard test remains the AGID because of its simplicity and low cost. The AGID has been demonstrated to be a useful test for routine herd testing in control programs for the eradication of BLV infection in closed dairy herds (Mammerickx, M. et al., (1978) *Ann. Rech. Vet.* 9, 885; Van Der Maaten, M.J. and Miller, J.M. (1979) *Journal of American Veterinary Medical Association*, 175, 1287). However, since BLV infection is subclinical and scheduled blood testing is required to control this disease and for certification of disease free status, many livestock owners do not submit to the cost of routine testing. As well, samples are usually sent to local laboratories where the AGID test results are not routinely available for a minimum of 48 hours.

As there is often considerable delay in obtaining test results there is a need for a simple and better test which could be utilized in situations where results are required as quickly as possible. Such circumstances often exist in sales barns or in calving situations in herds practicing colostrum substitution from BLV free cows. The methodology of the invention can be performed within one hour on samples such as serum or milk.

The test according to this invention is not intended to completely replace laboratory testing but if used on a routine basis it can be the best indicator of current herd status and a powerful tool to assist in herd management for the control and elimination of bovine leukemia virus infection or other infectious diseases. It is the purpose of this invention to be a relatively simple, low-cost, on-site test to monitor cattle and other animals for the presence of antibodies indicating exposure to particular infectious agents. In the instance of bovine leukemia virus the presence of antibodies to the virus has a strong positive correlation with ongoing BLV infection. This invention is a useful tool to determine the infectivity status of cows for purpose or to determine if colostrum replacement should be implemented. It is not the purpose of this test to replace veterinary certification but to assist in the monitoring of herds for the maintenance or development of pathogen-free status.

While the inventive test could be used by qualified experts to certify disease status, lay persons would be equally capable of using this invention to monitor disease and implement control procedures in livestock.

SUMMARY OF THE INVENTION

According to an aspect of the invention a method is provided for the detection of the presence of anti-viral or anti-bacterial antibodies in a specimen comprising:

contacting said specimen with solid phase support dipstick having attached thereto suitable antigen-binding material upon which viral antigens or bacterial antigens are bound, said antigens being capable of forming immuno-complexes with the antibodies which may be present in the specimen; and contacting said dipstick and any antibody-antigen immunocomplexes bound thereon with a fluid phase containing second antibodies capable of forming an immunocomplex with any specimen antibodies bound to said dipstick, said second antibodies having conjugated to them a means for effecting visual indication of the antigen-binding of the second antibodies to the specimen antibodies in the presence of suitable reactive agents.

According to another aspect of the invention a method is provided for the detection of the presence of anti-viral or anti-bacterial antibodies wherein the visual indication of second-antibody binding is achieved through conjugation of an enzyme to the second-antibody such that in the presence of a suitable substrate the enzyme will react chemically with the substrate to form a colour reaction product thereby indicating the presence of anti-viral or anti-bacterial antibodies in the specimen.

According to another aspect of the invention, a method is provided wherein the means for visually indicating binding of second- antibody to the specimen antibody is achieved by conjugating both an enzyme and a substrate to the secondary antibody such that at the time of antigen-binding of said second-antibody to the specimen antibody the enzyme and substrate are activated such that they chemically react to form a coloured reaction product thereby indicating the presence of anti-viral or anti-bacterial antibodies in the specimen.

According to another aspect of the invention a test kit is provided for the detection of anti-viral BLV antibodies in a fluid specimen which comprises as individual components:

a) a solid phase support dipstick having attached thereto a suitable antigen-binding substance having bound thereon one or more BLV antigens capable of forming immuno-complexes with the antibodies which may be present in the specimen; and b) a series of five sealed containers with removable closures containing in series:
  (i) an empty sterile container,
  (ii) a first wash solution,
  (iii) a solution containing enzyme conjugated to a second-antibody, said second-antibody being capable of forming an immunocomplex with the specimen antibodies,
  (iv) a second wash solution,
  (v) a substrate which reacts chemically with said enzymes so as to form a coloured reaction product thereby indicating the presence of anti-viral or anti-bacterial antibodies in said specimen;

said dipstick being attached to a removable closure of one of said containers, and with said dipstick optionally bearing a control test spot According to another aspect of the invention a method for using a solid phase support dipstick having attached thereto nitrocellulose suitable for binding proteins, for detecting the presence of anti-viral and anti-bacterial antibodies in a specimen wherein bound to the nitrocelloluse are viral antigens capable of forming immuno-complexes with antibodies which may be present in the specimen comprising first contacting said dipstick with the specimen and then contacting said dipstick and any antibody-antigen immuno-complexes bound thereon with a fluid phase containing second-antibodies capable of forming an immunocomplex with any specimen antibodies bound to dipstick, said second antibodies having conjugated to them a means for effecting visual indication of the antigen-binding of the secondantibodies to the specimen antibodies in the presence of suitable reactive agents where necessary.

According to another aspect of the invention a method of use is provided wherein the visual indication of second-antibody binding is achieved through conjugation of an enzyme to the second-antibody such that in the presence of a suitable substrate said enzyme will react chemically with the substrate to form a coloured reaction product thereby indicating the presence of anti-viral and anti-bacterial antibodies in said specimen.

According to another aspect of the invention, a method of use is provided wherein the means for visually indicating binding of second- antibody to the specimen antibody is achieved by conjugating both an enzyme and a substrate to the secondary antibody such that at the time of antigen-binding of said second-antibody to the specimen antibody the enzyme and substrate are activated such that they chemically react to form a coloured reaction product thereby indicating the presence of anti-viral or anti-bacterial antibodies in the specimen.

Other and further advantages and features of the invention will be apparent to those skilled in the art from the following detailed description thereof, taken in conjunction with the accompanying drawings.

BRIEF DESCRIPTION OF THE DRAWINGS

In the accompanying drawings:

FIG. 1 is a schematic illustration of a solid phase support in the form of a dipstick illustrating one preferred embodiment wherein two nitrocellulose (or nylon) antigen-binding matrices are attached thereon.

FIG. 2 illustrates the solid phase support dipstick as attached to the removable closure of a test tube in one preferred embodiment.

FIG. 3 represents a longitudinal section through the solid phase dipstick illustrating schematically the binding of the control antigens and specific antigens to the nitrocellulose or nylon antigen-binding matrix squares and the binding of the specimen antibodies to the specific antigens.

FIG. 4 is a longitudinal section through the solid phase dipstick illustrating schematically enzyme-labelled second-antibodies immunocomplexed to the specimen antibodies.

FIG. 5 is a longitudinal section through the solid phase dipstick illustrating schematically the addition of substrate molecules in the vicinity of the bound antibody molecules and the colored reaction product resulting from the enzyme-substrate chemical interaction.

DETAILED DESCRIPTION OF PREFERRED EMBODIMENTS

The principles of detecting anti-viral or anti-bacterial antibodies present in a specimen, such as serum or milk, are demonstrated in accordance with the following preferred embodiments of the invention.

The present invention is limited not only to the detection of bovine leukemia virus (BLV) but is also suitable for the detection of antibodies directed against most infectious agents. The detection of antibodies against BLV is but one preferred embodiment of the present invention. The present invention provides a method for the detection of antibodies in a specimen through the use of a solid phase support dipstick onto which is attached at least two matrix squares. One matrix square is used for the binding of non-specific control antigens and one to which has been attached a known viral or bacterial antigens These matrix squares are the sites of protein-binding and/or antigen-binding in this invention and are usually made of nitrocellulose; however, certain nylons and polyvinylidenes may also be suitable. Two commercial nylon products which may be suitable material for these antigen-binding sites are Genatran 45 (trade mark) and Immobilon PVDF (trade mark).

The antigen-binding matrix squares are attached onto a solid support dipstick which may be made of materials such as plastic or Mylar (trade mark). Through the use of this invention, it is possible that multiple disease specific antibodies could be identified by a single test through the incorporation of multiple matrix squares each containing different specific antigens at various positions on a single test strip, or on a single solid phase support dipstick.

This invention also provides for a test kit incorporating the use of a solid phase support dipstick. By the process of sequentially dipping the dipstick through the series of reagents provided in the kit the presence or absence of particular antibodies in a specimen can be simply and quickly ascertained. This kit is suitable for use by experts and lay persons alike. Similarly the kit is as suitable for use in a farmer's field as in a laboratory. The use of the present kit invention will permit the rapid serologic diagnosis of viral and bacterial diseases from body fluids such as blood, milk, urine, plasma and cerebrospinal fluid. As well, the kit composition could readily be altered to permit the detection of any class of antibodies: IgG, IgM or IgA. In particular one could use this kit to differentiate between acute and chronic stages of infectious diseases by using the appropriate second-antibody detection probes for recognizing either IgM or IgG antibodies.

The enzymes which are covalently bound to the second-antibodies react with substrates which yield a colour reaction product at the end of the enzyme-substrate reaction. In this way the presence of bound second-antibody can be readily detected thereby indicating the presence of antibodies in the specimen which are specific for the tested antigen. The technology incorporates well known ELISA techniques.

It is understood that the selection of appropriate enzymes and substrates and the appropriate reaction conditions would be known to one skilled in the art. Table 1 lists enzymes frequently used in immunochemistry technology. These enzymes remain active after being conjugated to immunoglobulin molecules. Each enzyme-substance pair reacts chemically to generate a colored reaction product. In addition there are alternative conjugates in which the enzyme and substrate are both conjugated into the second-antibody solution but the enzyme and substrate only react to form the colored reaction product after the second-antibody has bound to the specimen antibody.

TABLE 1

| Enzyme | Substrate[1, 2] |
| --- | --- |
| Alkaline Phosphatase | 5-bromo-4-chloro-3-indolyl-phosphate (in the presence of nitroblue tetrazolium) |
| Alkaline Phosphatase | naphthol AS-MX |
| Alkaline Phosphatase | AS-B1 phosphate (in the presence of Fast Red or Fast Blue) |
| Horseradish Peroxidase | 4-chloro-1-naphthol (in the presence of hydrogen peroxide) |
| Horseradish Peroxidase | 3,3' Diaminobenzidine (in the presence of hydrogen peroxide) |
| Horseradish Peroxidase | 3-amino-9-ethylcarbazole (in the presence of hydrogen peroxide) |
| β-Galactosidase | 5-bromo-4-chloro-3-indolyl-β-D-galactopyranoside |

[1] where required, to achieve the desired chemical reaction, auxiliary reagents are set out in parentheses.
[2] note that in these examples the substrate is added in a separate step from the enzyme.

In accordance with a preferred aspect of the invention, bovine leukemia virus is prepared by propagation in BLV-Bat$_2$ cell/culture or other suitable virus producing cell line as described by Graves and Ferrer (1976) (Graves, C. D. and Ferrer, J. F., Cancer Research 36:4152-4159,1976). The supernatant is collected from the BLV-Bat$_2$ cell cultures and the BLV virus is purified by differential centrifugation. After differential centrifugation are solubilized in phosphate buffered saline (pH 7.4).

In a similar fashion, non-infected supernatant from fetal lamb kidney cells is collected as a control for the detection of non-specific background. The resuspended viral pellet is titred against control positive and negative sera to determine the optimal level of dilution. Virus is neutralized by the addition of (0.01%) polyethyleneglycol (PEG). The control protein preparation from the non-infected TbILu cell cultures is diluted to give the same protein concentration as the titrated virus preparation.

The viral antigens present in the virus solution are placed on the lower antigen-binding matrix square on the solid phase support dipstick so as to form a small spot or dot. In a similar manner the control antigen is placed above the viral antigens on the uppermost antigen-binding nitrocellulose or nylon matrix square to form a second spot or dot. The nitrocellulose matrices are allowed to air dry for 10 to 15 minutes and the remaining binding sites on the nitrocellulose matrices are blocked using a solution of 3% gelatin at 37° C. for 30 to 60 minutes.

Once the antigens are bound, the solid phase support dipstick is placed in a test tube or similar receptacle to which is added the specimen sample of serum or milk. The specimen sample is allowed to react with the bound antigens on the dipstick for 15 minutes at room temperature. The dipstick is then removed and gently rinsed in PBS, containing 0.02% polyoxyethylenesorbitan monolaurate [TWEEN 20 (trademark)], for 5 minutes.

The solid phase support dipstick is removed from the wash solution and placed in another tube containing highly diluted, affinity purified antibovine immunoglobulin conjugated to alkaline phosphatase or another suitable enzyme and left for 15 minutes at room temperature. The dipstick is then removed from the second-antibody solution and placed in a container of wash solution for a further 5 minutes at room temperature.

Upon removal from the wash solution the dipstick is placed in a final tube of commercially prepared and premixed chromogen solution or other suitable substrate solution. A strong positive reaction may be visible within 3 to 5 minutes, a weak positive reaction may take 10 to 15 minutes to develop. Reactions requiring longer than 20 minutes are equivocal and should be repeated 21 to 30 days later.

The dipstick is assessed for a positive reaction by simple visual comparison of the control (upper spot) with the positive (lower spot). If the positive spot is darker than the control, then the test is considered positive. Tests should always be performed with positive and negative controls.

In accordance with another preferred aspect of the invention is a test kit comprising a series of sealed containers with removable closures containing the necessary reagents to permit the performance of this methodology at any location. In particular such a kit would be of great assistance for routine testing in field situations.

Such a kit would contain an empty sterile container into which a specimen sample would be placed. It would also contain the necessary wash solutions which according to one preferred embodiment of the invention are 0.05% TWEEN 20 in phosphate buffered saline, pH 7.4. The kit would also include a container containing a solution of enzyme conjugated to a second-antibody, this labelled second-antibody being capable of forming an immunocomplex with the specimen antibodies. The kit would also include a container containing the appropriate substrate which would react chemically with the enzyme to form a coloured reaction product thereby indicating the presence of anti-viral antibodies in the specimen. When the dipstick is removed from the substrate solution, if there are antibodies present in the specimen capable of immunocomplexing with the antigen on the dipstick, the spot where the antigen was originally adsorbed to the nitrocellulose will be coloured and will appear a darker colour than the antigen spot where the control antigens were adsorbed.

Tests should always be performed with positive and negative serum controls as supplied for accurate field assessment. The positive and negative antigen controls would already be present on the dipstick as included in the test kit.

In accordance with another preferred aspect of the invention, is a method for using a solid phase support dipstick for the detection of the presence of anti-viral antibodies, and in particular the method for using such a dipstick in a rapid test field kit, as described.

Referring now to the drawings, FIG. 1 is a schematic illustration of a solid phase support 2 in the form of a dipstick illustrating one preferred embodiment wherein two nitrocellulose or nylon antigen-binding matrix squares 4 and 6 are attached thereon.

FIG. 2 illustrates the solid phase support dipstick 2 as attached to the removable closure 10 of a test tube 8 at a point of attachment 12 containing a specimen sample 7.

FIG. 3 is a longitudinal section through the solid phase support dipstick 2, as viewed from the side, illustrating schematically the binding of non-specific control antigens 12 to one of the antigen-binding matrix squares 4 and the binding of specific antigens to another matrix square 6. FIG. 3 also illustrates the specific binding of the specimen antibodies 16 to only the specific antigen 14 and not to the control antigens 12.

FIG. 4 is a longitudinal section through the solid phase support dipstick 2 illustrating schematically the specific binding of the enzyme-labelled second-antibodies 18 to only the specimen antibodies 16 and not to the control antigens 12. The second-antibodies 18 are labelled with an enzyme 20.

FIG. 5 is a longitudinal section through the solid phase dipstick 2 illustrating schematically the addition of substrate 22 into the specimen sample 7. The substrate 22 and enzyme 20 chemically react to form a colored reaction product 24. This colored reaction product 24 will be localized to that area where the enzyme is located on the solid phase support 2 and settle into the antigen-binding nitrocellulose or nylon matrix as at 26 thereby leaving a colored spot on the matrix square indicative of a positive reaction.

Further details of the preferred embodiments of the invention will be understood from the following Examples which are understood to be non-limiting with respect to the appended claims.

EXAMPLE 1

Preparation of Viral and Control Proteins

Virus was propagated in BLV-Bat$_2$ cells as described by Graves and Ferrer (1976) Cancer Research, Vol. 36, pp 4152-4159. After seven days, supernatant, was collected in 500 ml amounts and frozen (−20° C.) and cells passaged. Virus was purified by differential centrifugation as follows. One liter of thawed supernatant was clarified by centrifugation at 4,000 g for 10 minutes at 4° C. Concentration by ultracentrifugation at 40,000 g for 45 minutes in a SW27 rotor (Beckman L6) at 4° C. was performed repeatedly until all clarified supernatant had been concentrated to one pellet. Pellets were solubilized in 1 ml of PBS (0.01 M sodium phosphate, pH 7.2, NaCl 0.15 M). Non-infected supernatant from TbILu cells was prepared in a similar manner as a control for detection of non-specific background. Several two-fold dilutions of 100 ul of resuspended viral pellet was plated over F-81 indicator cell line, and the number of infectious units determined by syncytial induction. Final dilution of resuspended virus was standardized to give approximately $1 \times 10^8$ infectious units per ml. Protein determination was by the Lowrey technique. The control protein preparation was diluted to give the same protein dilution as the virus preparation.

EXAMPLE 2

Preparation of Test Strips

Preparation of nitrocellulose strips was performed as follows: 40×0.5 cm strips of high quality nitrocellulose or nylon equivalent were placed over empty wells of an 96 well multititre dot blot suction apparatus (BIO-RAD). Ten ml of virus solution was placed over the bottom well of each strip undersection. Leaving a one well space, 10 ul of the control preparation was placed above the virus positive dot. Allowing 10-15 minutes to dry, each strip was numbered and blocked in 3% gelatin. Strips were removed after 30 minutes, placed between parafilm freeze-dried and vacuum wrapped until use.

EXAMPLE 3

Performing the Rapid Screening Test

Nitrocellulose strips are placed in small 3 ml tubes containing test sample (whole serum or milk) for 15 minutes at room temperature. Strips are then removed and gently rinsed under slow running water for 30 seconds, and placed immediately in a second 3 ml tube containing wash solution (0.05% TWEEN 20 in phosphate buffered saline, pH 7.4) for 5 minutes. Following this, strips are then placed in a third tube containing an equal mixture of highly diluted (1/500 to 1/1000) affinity purified mixture of antibovine IgG and IgM conjugated to alkaline phosphatase. This reaction is allowed to take place for another 15 minutes at room temperature. This is again rinsed briefly and placed in a tube of wash solution for 5 minutes. Finally strips are placed in a fourth tube of commercially prepared and premixed chromogen solution. A positive reaction is visible within 3 to 5 minutes. Reactions requiring longer than this are equivocal and should be repeated 21 to 30 days later. Strips are assessed for a positive reaction by simple visual comparison of the control (upper dot) with the positive (lower dot). If the positive dot is darker than the control, then the test is considered positive. Tests should always be performed with positive and negative serum controls.

Although preferred embodiments of the invention have been described herein in detail, it will be understood by those skilled in the art that variations may be made thereto without departing from the spirit of the invention or the scope of the appended claims.

We claim:

1. A test kit for the detection of antibodies to bovine leukemia virus in cow's milk which comprises as individual components:
   (a) a solid phase support dipstick having attached thereon at least two-spaced apart suitable antigen-binding substances;
   a first of said antigen-binding substances having bound thereon one or more bovine leukemia virus antigens capable of forming immuno-complexes with the antibodies which may be present in the specimen, and
   a second of said antigen-binding substances having bound thereon one or more control antigens for the detection of non-specific background;
   (b) a series of five sealed containers with removable closures containing in series:
      (i) an empty sterile container,
      (ii) a first wash solution,
      (iii) a solution containing enzyme conjugated to a second-antibody, said second-antibody being capable of forming an immunocomplex with the specimen antibodies,
      (iv) a second wash solution,
      (v) a substrate which reacts chemically with said enzymes so as to form a colored reaction product thereby indicating the presence of anti-viral antibodies in said specimen;
   said dipstick being attached to a removable closure of one of said containers.

2. A kit according to claim 1 wherein said solid phase support dipstick is made of plastic.

3. A kit according to claim 2 wherein said antigen-binding substances are selected from the group consisting of nitrocellulose, polyamides and polyvinylidenes.

4. A kit according to claim 2 wherein said antigen-binding substance is nitrocellulose.

5. A kit according to claim 4 wherein said dipstick is prepared by mounting at least two nitrocellulose matrix square onto a plastic strip.

6. A kit according to claim 4 wherein said wash solution is PBS.

7. A kit according to claim 4 wherein said wash solutions are mixtures of polyoxyethylenesorbitan monolaurate and PBS.

8. A kit according to claim 4 wherein said enzyme is alkaline phosphatase.

9. A kit according to claim 8 wherein said substrate is selected from the group consisting of 5-bromo-4-chloro-3-indolyl-phosphate in the presence of nitroblue tetrazolium, naphthal AS-MX and AS-B1 phosphate in the presence of Fast Red or Fast Blue.

10. A kit according to claim 4 wherein said enzyme is horeradish peroxidase.

11. A kit according to claim 4 wherein said enzyme is β-galactosidase and said substrate is 5-bromo-4-chloro-3-indolyl-β-D-galactopyranoside.

12. A kit according to claim 4 wherein said second-antibody is monoclonal.

13. A kit according to claim 4 wherein said second-antibody is polyclonal and affinity purified.

14. A kit according to claim 12 wherein said monoclonal second-antibody specifically recognizes the IgG immunoglobulin molecules of the animal specie from which the specimen was taken.

15. A kit according to claim 12 wherein said monoclonal second-antibody specifically recognizes the IgA immunoglobulin molecules of the animal specie from which the specimen was taken.

16. A kit according to claim 13 wherein said monoclonal second-antibody specifically recognizes the IgM immunoglobulin molecules of the animal specie from which the specimen was taken.

17. A kit according to claim 13 wherein said polyclonal second-antibody specifically recognizes the IgG immunoglobulin molecules of the animal specie from which the specimen was taken.

18. A kit according to claim 13 wherein said polyclonal second-antibody specifically recognizes the IgA immunoglobulin molecules of the animal specie from which the specimen was taken.

19. A kit according to claim 13 wherein said polyclonal second-antibody specifically recognizes the IgM immunoglobulin molecules of the animal specie from which the specimen was taken.

20. A kit according to claim 4 wherein the bovine leukemia virus antigens are bound to the nitrocellulose so as to form a spot of antigen concentration at the distal end of the dipstick.

* * * * *